(12) United States Patent
Curry et al.

(10) Patent No.: US 9,345,408 B2
(45) Date of Patent: May 24, 2016

(54) ORAL SCREENING TOOTHBRUSH

(71) Applicant: Beam Technologies, LLC, Louisville, KY (US)

(72) Inventors: Alexander D. Curry, Louisville, KY (US); Daniel E. Dykes, Louisville, KY (US); Alex X Frommeyer, Louisville, KY (US)

(73) Assignee: BEAM TECHNOLOGIES, LLC, Louisville, KY (US)

( * ) Notice: Subject to any disclaimer, the term of this patent is extended or adjusted under 35 U.S.C. 154(b) by 126 days.

(21) Appl. No.: 14/214,734

(22) Filed: Mar. 15, 2014

(65) Prior Publication Data

US 2014/0272768 A1    Sep. 18, 2014

Related U.S. Application Data

(60) Provisional application No. 61/790,298, filed on Mar. 15, 2013.

(51) Int. Cl.
*A61B 5/00* (2006.01)
*A46B 15/00* (2006.01)

(52) U.S. Cl.
CPC ............ *A61B 5/0088* (2013.01); *A46B 15/0034* (2013.01); *A46B 15/0055* (2013.01); *A46B 2200/1066* (2013.01)

(58) Field of Classification Search
CPC ............. A61B 5/0088; A61B 15/0034; A61B 15/0055; A61B 2200/1066
See application file for complete search history.

(56) References Cited

U.S. PATENT DOCUMENTS

| | | | | |
|---|---|---|---|---|
| 5,894,620 A | * | 4/1999 | Polaert ................ | A61B 5/0088 15/22.1 |
| 2012/0295216 A1 | * | 11/2012 | Dykes ............................ | 433/27 |
| 2014/0033034 A1 | * | 1/2014 | Patel .................. | A46B 15/0006 715/716 |

* cited by examiner

*Primary Examiner* — Shay Karls
(74) *Attorney, Agent, or Firm* — Alexander D. Curry (57) ABSTRACT

An oral screening toothbrush is provided for screening for oral diseases such as oral cancer and dental caries. The toothbrush emits blue light into the oral cavity and captures an image of the reflection of blue light. Image processing techniques are used to analyze the images to screen for oral diseases. Further, the toothbrush is comprised in a system including a data transfer medium (i.e. "smartphone") and the Cloud, which allows for data transfer between multiple platforms from the toothbrush. The oral screening toothbrush and extended system provide for in-home oral screening and interaction with health professionals.

19 Claims, 5 Drawing Sheets

ORAL SCREENING TOOTHBRUSH

CROSS-REFERENCE TO RELATED APPLICATIONS

This application claims priority to U.S. Provisional Application No. 61/790,298 filed on Mar. 15, 2013.

BACKGROUND OF THE INVENTION

This invention relates to a toothbrush for screening for oral diseases outside of the dental office. In particular, the invention relates to a toothbrush for screening for oral diseases such as oral cancer and dental caries.

Oral screening is currently performed in the dental office during regular dental visits. An inherent problem exists in that dental visits are relatively infrequent. Dental visits are recommended to occur every six months but often happen less frequently than recommended. This leaves a large amount of time for oral diseases to develop without proper screening. Current methods lack the frequency of screening that is required to adequately identify oral disease in the early stage of development.

BRIEF SUMMARY OF THE INVENTION

This invention aims to provide an oral screening toothbrush to identify oral disease. The toothbrush emits blue light into the oral cavity and captures an image of the reflection of blue light. Image processing techniques are used to analyze images to screen for oral diseases. Additionally, the oral screening toothbrush is comprised in a system including a data transfer medium and the Cloud to allow data transfer to multiple platforms from the toothbrush.

Accordingly several advantages are to provide an oral screening toothbrush, to provide means for screening for oral disease in an in-home setting, and to provide a system for transferring the data between multiple platforms. Still further advantages will become apparent from a study of the following descriptions and the accompanying drawings.

DETAILED DESCRIPTION OF THE INVENTION

The oral screening toothbrush is encompassed in a plurality of embodiments that shall be discussed in the present section.

A plurality of embodiments comprises an oral screening toothbrush. A toothbrush is an oral health care implement used for the cleaning of teeth and gingiva, more commonly referred to as gums. The toothbrush is operated in the oral cavity of a human being characterized as the first portion of the alimentary canal that receives food and saliva, and containing a mucous membrane epithelium lining referred to as the oral mucosa. The oral cavity is further characterized as having alveolar arches typically containing teeth, which are either natural, synthetic, or a combination thereof, and used primarily for the preparatory chewing of food for digestion.

Figure 1:
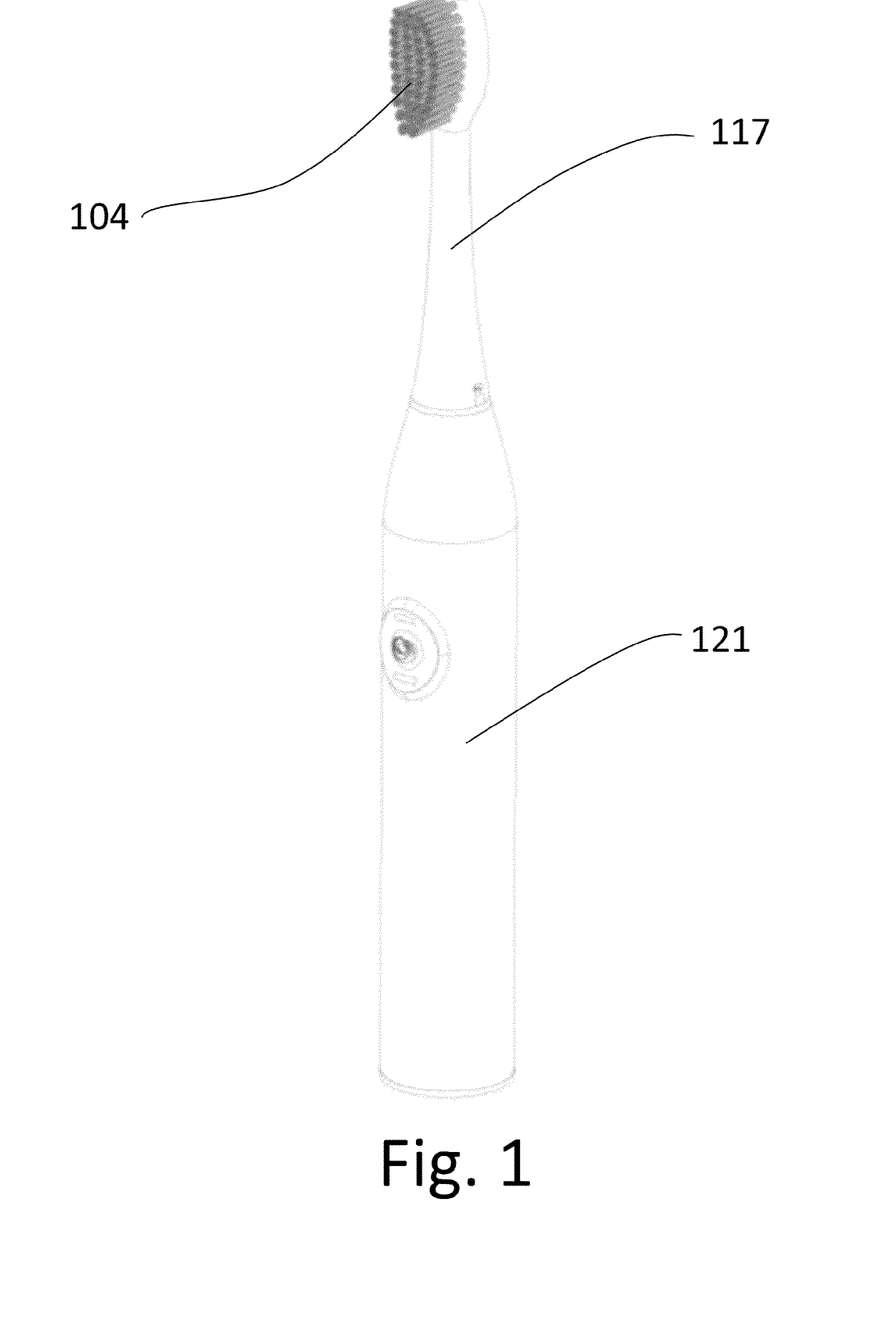
FIG. 1 is a perspective front view of an oral screening toothbrush as described in multiple embodiments and alternatives.

Referring to FIG. 1, a toothbrush comprises a brush head 104 consisting of a plurality of bristles arranged into compact clusters, often referred to as tufts, mounted onto the brush head. Accordingly, the tufts are often mounted in an intentional pattern to facilitate cleaning of teeth and gums. A toothbrush comprises a neck 117 that extends proximally from the brush head. A toothbrush further comprises a handle 121 that extends proximally from the neck and is used for grasping and movement of the toothbrush. The bristles of the toothbrush are commonly manufactured from either a natural material, synthetic material, or a combination thereof. One example of a natural bristle material is animal hair. An example of a typical synthetic bristle material is Nylon.

In some further embodiments, the oral screening toothbrush comprises a flosser. A flosser is an oral health care implement used for the removal of good and dental plaque from teeth, especially between teeth and other places a toothbrush cannot effectively clean. A flosser comprises a flosser head having two parallel protrusions with space between them such that a length of dental floss can be placed between the two protrusions. The dental floss is, most often, held taut by the two protrusions to facilitate proper cleaning. Two common orientations exist for the protrusions in relation to the major axis of a handle including F-shaped wherein the protrusions are generally perpendicular to the major axis of the handle; and the Y-shaped wherein the protrusions are generally parallel to the major axis of the handle.

Inherently, a toothbrush has an associated motion when in use, which is characterized as either manually driven (i.e. manual toothbrush) or electromechanically driven (i.e. powered toothbrush). A manually driven motion is regarded as a motion generated by the user by his/her own power. Conversely, an electromechanically driven motion is characterized as a motion generated by electrical power which is converted to mechanical power used to create the specified electromechanically driven motion. In some embodiments, the electromechanically driven motion is a side-to-side oscillating motion also referred to as vibratory motion. Often, the vibratory motion is generated by an electric motor with an eccentric weight on the drive shaft of the electric motor. In other instances, the vibratory motion is generated by an electrically conductive coil around the outside of a magnetic mass, such that when an alternating current is applied to the coil, the magnetic mass oscillates causing vibration of the toothbrush. In other embodiments, the electromechanically driven motion is a rotation-oscillation motion wherein the head rotates either clockwise or counter-clockwise and then rotates in the opposite direction of the first rotation. Additionally, a portion of the brush head may move in a translational motion to provide additional cleaning.

The oral screening toothbrush further comprises a data processing unit having at least one collector, a storage medium, and at least one processor, wherein the collector, storage medium, and processor, respectively, collect, store, and process data. Accordingly, the data processing unit is chosen from the group microprocessor, microcontroller, field programmable gate array (FPGA), digital signal processing unit (DSP), application specific integrated circuit (ASIC), programmable logic, and combinations thereof.

Additionally, in some embodiments, the collector of the data processing unit is an electrically conductive wire, wherein the electrically conductive wire receives the electrical output of various sensors.

Moreover, the storage medium of the data processing unit is comprised of volatile memory and non-volatile memory, wherein volatile memory is used for short-term storage and processing, and non-volatile memory is used for long-term storage. Accordingly, volatile memory is chosen from the group random-access memory (RAM), dynamic random-access memory (DRAM), double data rate synchronous dynamic random-access memory (DDR SDRAM), static random-access memory (SRAM), thyristor random-access memory (T-RAM), zero-capacitor random-access memory (Z-RAM), and twin transistor random-access memory (TTRAM). Non-volatile memory is chosen from the group read-only memory (ROM), programmable read-only memory (PROM), erasable programmable read-only memory (EPROM), electrically erasable programmable read-only memory (EEPROM), flash memory, ferroelectric random-access memory (FeRAM), magnetoresistive random-access memory (MRAM), phase-change memory (PRAM), conductive-bridging random-access memory (CBRAM), silicon-oxide-nitride-oxide-silicon memory (SONOS), resistive random-access memory (RRAM), racetrack memory, nano-random-access memory (NRAM), and Millipede memory.

The processor of the data processing unit is chosen from the group microprocessor and micro controller.

Optionally, the toothbrush further comprises at least one transceiver, such that the data can be extracted to be used by another medium. The data is packaged as at least one signal and transmitted to another medium. The transceiver is chosen form the group universal serial bus (USB), serial port, wired Ethernet port, radio frequency, microwave communication, infrared short-range communication, near field communication, and Bluetooth®.

In some embodiments, the oral screening toothbrush further comprises at least one light-emitting diode (LED) that emits light into the oral cavity. Optionally, the light-emitting diode emits blue light at a wavelength of 450-495 nanometers. The blue light enters the oral cavity and is reflected from all of the surfaces in the oral cavity. The reflection of blue light differs between normal and abnormal tissue within the oral cavity. The data processing unit of the toothbrush controls the light-emitting diode including its intensity and activation. Optionally, multiple light-emitting diodes are used in a clustered configuration to provide greater luminescence of the oral cavity.

Figure 2:
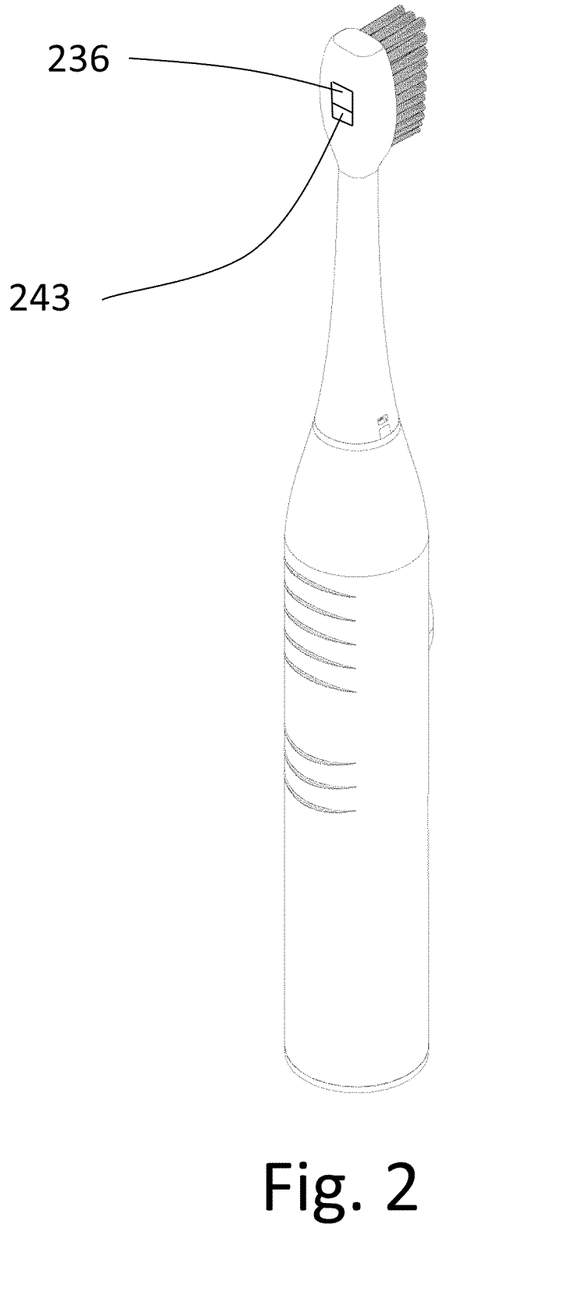
FIG. 2 is a perspective rear view of an oral screening toothbrush with the light-emitting diode and photo detector located in the brush head as described in multiple embodiments and alternatives.

Referring now to FIG. 2, at least one light-emitting diode 236 is comprised in the brush head 104 of the toothbrush such that blue light can be emitted from the section of the toothbrush currently placed in the oral cavity. FIG. 2 shows the blue light being emitted from the side opposite of the side that contains a plurality of bristles.

In some embodiments, the light-emitting diode comprised in the brush head 104 is oriented such that the blue light is emitted from the side that contains a plurality of bristles.

Figure 3:
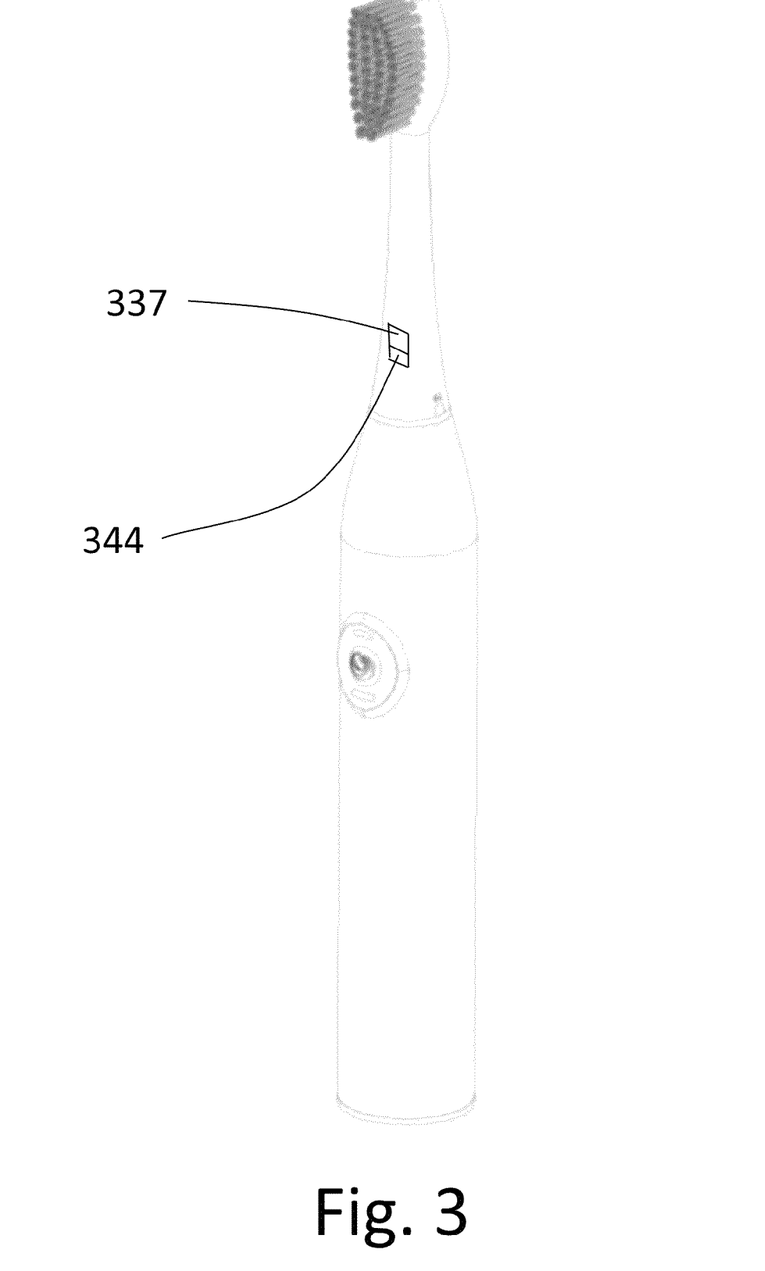
FIG. 3 is a perspective front view of an oral screening toothbrush with the light-emitting diode and photo detector located in the neck as described in multiple embodiments and alternatives.

As shown in FIG. 3, at least one light-emitting diode 337 is comprised in the neck 117 of the toothbrush such that the neck 117 can be positioned above the oral cavity and emits blue light into the oral cavity. This action provides for a deliberate activity of placing the toothbrush in position for blue light to be emitted from the neck 117 and enter the oral cavity.

Figure 4:
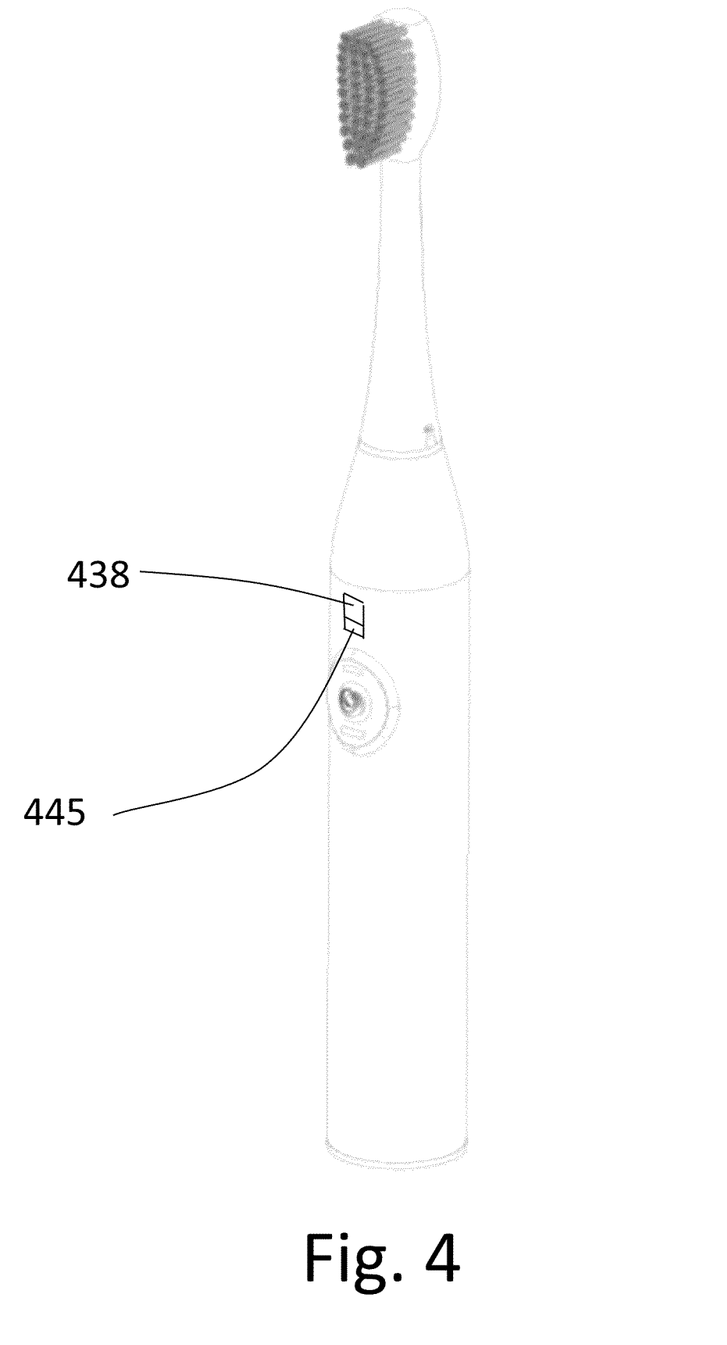
FIG. 4 is a perspective front view of an oral screening toothbrush with the light-emitting diode and photo detector located in the handle as described in multiple embodiments and alternatives.

Referring now to FIG. 4, due to size constraints of the brush head, at least one light emitting diode 438 is comprised in the handle 121 of the toothbrush. In this configuration, an optical fiber, or waveguide, is further comprised in the toothbrush, wherein one end of the optical fiber is coupled to the emission surface of the light emitting diode. Accordingly, the second end of the optical fiber is coupled to the external surface of the toothbrush such that the blue light is easily emitted from the toothbrush.

Optionally, the second end of the optical fiber coupled to the external surface of the brush head 104 such that the light-emitting diode is comprised in the handle 121 of the toothbrush and the blue light is emitted from the brush head 104 of the toothbrush. This configuration provides an optimum form factor that does not require significant enlargement of the brush head beyond industry norms.

In some embodiments, the oral screening toothbrush further comprises at least one photo detector that receives the emitted light that is reflected from the surfaces of the oral cavity. The photo detector captures an image of the oral cavity showing the reflected blue light on the tissues of the oral cavity. The photographic data is transmitted from the photo detector to the data processing unit of the oral screening toothbrush.

The photo detector is chosen from the group active pixel sensor, charge-coupled device, reverse-biased LED, photoresistor, photovoltaic cell, phototransistor, and quantum dot photo detector. An active pixel sensor consists of an integrated circuit with an array of pixel sensor, wherein each pixel contains a light sensor and an active amplifier. A common type of active pixel sensor is a complementary metal-oxide-semiconductor (CMOS) sensor. A charge-coupled device comprises capacitors that are biased above the threshold for inversion when image acquisition begins, which allows for the conversion of incoming photons into electron charges. The charge-coupled device then reads the electron charges into an image.

A reverse-biased LED operates under the reverse principle of an LED light source. Instead electrical current being passed through the diode to produce light, the reverse-biased LED receives light and converts the light into an electrical signal, thus allowing the presence of light to be detected. The reverse-biased LED provides an economical solution to simple photo detectors. Similarly, a photoresistor is made of a high resistance semiconductor that exhibits a decreasing resistance as incident light intensity increases, thus detecting the presence of light. Additionally, a photovoltaic cell converts light energy into direct current electricity such that the detection of light is accomplished by detecting the increased electrical power. A phototransistor is a bipolar transistor with a transparent case that allows light to reach the base-collector junction, which amplifies the current allowing for light detection. Lastly, a quantum dot photo detector operates similar to other semiconductor photo detectors but has electronic characteristics closely related to the size and shape of an individual crystal, thus creating a larger band gap in the semiconductor. Quantum dot photo detectors can be integrated with a large variety of substrates allowing for photo detection in very small spaces.

Optionally, the photo detector 243 is located in the brush head 104 of the toothbrush such that it is in close enough proximity to the light-emitting diode 236 to capture an image while blue light is emitted into the oral cavity, as shown in FIG. 2. Alternatively, the photo detector 344 may be located in the neck 117, as shown in FIG. 3, of the toothbrush such that it is in close enough proximity to the light-emitting diode 337 to capture an image while blue light is emitted into the oral cavity. Optionally, the photo detector 445 is located in the handle 121 of the toothbrush, as shown in FIG. 4, and coupled to the first end of at least one optical fiber. The second end of the optical fiber is coupled to the exterior surface of the toothbrush. In some embodiments, the second end of the optical fiber is coupled to the exterior surface of the brush head 104.

In some embodiments, the photographic data transmitted by the photo detector to the data processing unit undergoes image processing to analyze the image for certain oral conditions. One condition that is screened for is oral cancer, wherein image processing techniques are used to locate dark spots within the oral cavity from the photographic data. Abnormal tissues within the oral cavity reflect blue light as darker spots then normal tissue. Therefore, dark spots indicate locations within the oral cavity that should be examined in greater detail by a health professional. Another condition that is screened for is dental caries, wherein image processing techniques identify teeth within the oral cavity and analyze teeth separate from the remainder of the oral cavity. Dental caries are identified by dark spots on teeth such that a cavity is a hole in the tooth and does not reflect light at the same intensity as the intact enamel on a tooth.

Figure 5:
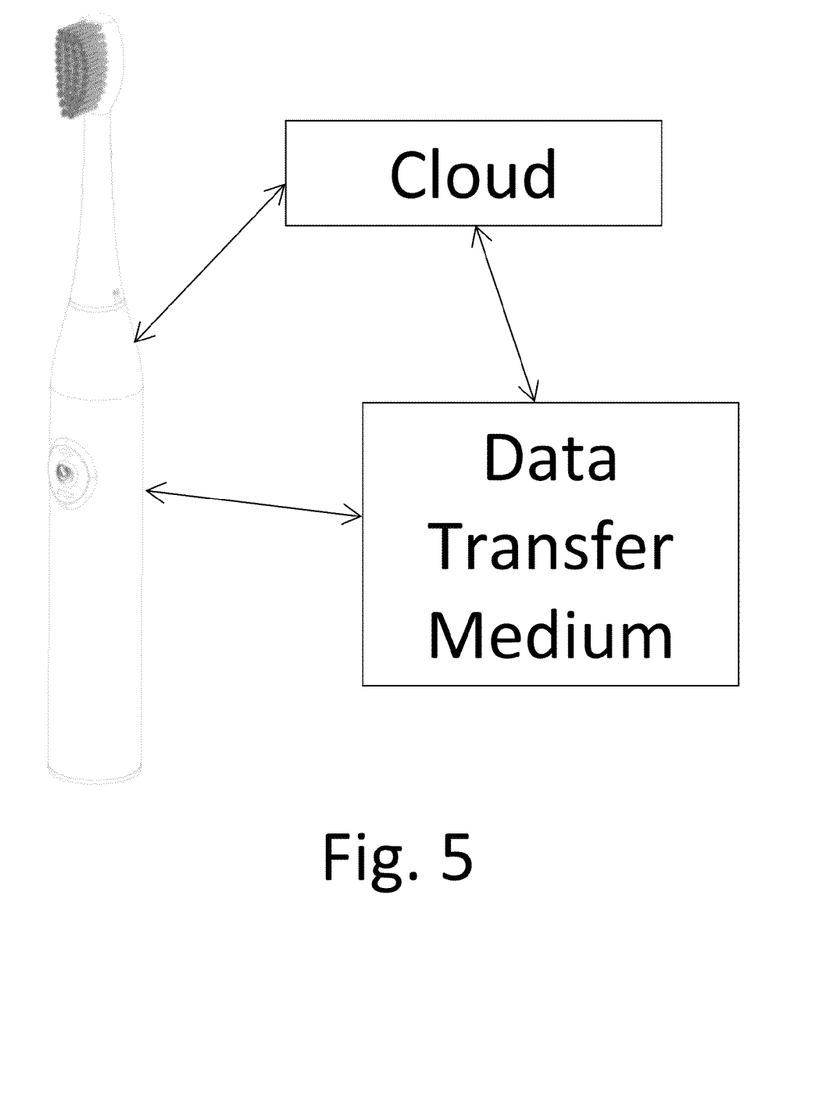
FIG. 5 is a schematic view of an oral screening toothbrush system as described in multiple embodiments and alternatives.

Referring now to FIG. 5, the photographic data is transmitted via the transceiver to a data transfer medium or the Cloud. In this configuration, image processing and analysis of the photographic images is performed using a data transfer medium or other device that has access to the Cloud. This configuration provides the ability to transmit the photographic data to a health professional directly and also keep a record of oral health screenings. Optionally, the data processing unit of the oral screening toothbrush stores a record of oral screenings that are transmitted to a data transfer medium or the Cloud for eventual transmission to a health professional for analysis.

In some embodiments, the oral screening toothbrush including variations described herein is comprised in a system that allows a user to view and analyze the photographic data via a data transfer medium, such as a "smartphone", and/or a network storage device, often known as the "cloud" and hereinafter referred to as the Cloud. Embodiments of the oral screening toothbrush comprised in this system include the transceiver described previously. Accordingly, the system allows the toothbrush to transfer data to the data transfer medium and/or the Cloud. Additionally, the data transfer medium may transfer said data to the Cloud for display and manipulation on further data transfer mediums connected to said Cloud. Alternatively, the Cloud may transfer said data to the data transfer medium.

In some embodiments, the data transfer medium comprises a receiver, a transmitter, a data processing unit, and a display. Accordingly, the data processing unit is chosen from the group microprocessor, microcontroller, field programmable gate array (FPGA), digital signal processing unit (DSP), application specific integrated circuit (ASIC), programmable logic, and combinations thereof. The data processing unit comprises a collector, storage medium, and a processor.

Moreover, the storage medium of the data processing unit is comprised of volatile memory and non-volatile memory, wherein volatile memory is used for short-term storage and processing, and non-volatile memory is used for long-term storage. Accordingly, in some embodiments, volatile memory is chosen from the group random-access memory (RAM), dynamic random-access memory (DRAM), double data rate synchronous dynamic random-access memory (DDR SDRAM), static random-access memory (SRAM), thyristor random-access memory (T-RAM), zero-capacitor random-access memory (Z-RAM), and twin transistor random-access memory (TTRAM). Optionally, in some embodiments, non-volatile memory is chosen from the group read-only memory (ROM), programmable read-only memory (PROM), erasable programmable read-only memory (EPROM), electrically erasable programmable read-only memory (EEPROM), flash memory, ferroelectric random-access memory (FeRAM), magnetoresistive random-access memory (MRAM), phase-change memory (PRAM), conductive-bridging random-access memory (CBRAM), silicon-oxide-nitride-oxide-silicon memory (SONOS), resistive random-access memory (RRAM), racetrack memory, nano-random-access memory (NRAM), and Millipede memory.

Further still, the processor of the data processing unit is chosen from the group microprocessor and microcontroller.

Additionally, the receiver of the data transfer medium is chosen from the group universal serial bus (USB), serial port, wired Ethernet port, radio frequency, microwave communication, infrared short-range communication, near field communication, and Bluetooth. Often, the receiver of the data transfer medium receives at least one signal from the transceiver of the toothbrush.

Optionally, the data transfer medium is chosen from the group personal computer, tablet computer, mobile phone (i.e. "smartphone"), television, dedicated system, charging station, network router, and web-enabled server.

Optionally, the transmitter of the data transfer medium is chosen from the group universal serial bus (USB), serial port, wired Ethernet port, radio frequency, microwave communication, infrared short-range communication, near field communication, and Bluetooth.

Additionally, the display of the data transfer medium converts signals into user-readable formats.

In some embodiments, the Cloud is connected to a network, wherein the network is chosen from the group Internet or intranet such that an intranet is a network managed and accessed by an internal organization and is not accessible to the outside world. The network is utilized by the Cloud for receiving and transmitting data. The mode for receiving and transmitting data through the network is chosen from the group universal serial bus (USB), serial port, wired Ethernet port, radio frequency, microwave communication, infrared short-range communication, near field communication, and Bluetooth.

Additionally, the Cloud processes data using at least one microprocessor, at least one microcontroller, or a combination thereof. The storage of data is comprised of volatile memory and non-volatile memory, wherein volatile memory is used for short-term storage and processing, and non-volatile memory is used for long-term storage. Accordingly, volatile memory is chosen from the group random-access memory (RAM), dynamic random-access memory (DRAM), double data rate synchronous dynamic random-access memory (DDR SDRAM), static random-access memory (SRAM), thyristor random-access memory (T-RAM), zero-capacitor random-access memory (Z-RAM), and twin transistor random-access memory (TTRAM). Optionally, non-volatile memory is chosen from the group read-only memory (ROM), programmable read-only memory (PROM), erasable programmable read-only memory (EPROM), electrically erasable programmable read-only memory (EEPROM), flash memory, ferroelectric random-access memory (FeRAM), magnetoresistive random-access memory (MRAM), phase-change memory (PRAM), conductive-bridging random-access memory (CBRAM), silicon-oxide-nitride-oxide-silicon memory (SONOS), resistive random-access memory (RRAM), racetrack memory, nano-random-access memory (NRAM), and Millipede memory.

The Cloud, optionally, is a network server primarily used for storing and processing data. Optionally, the Cloud is comprised of more than one network server such that the network servers operate in conjunction to increase the storing and processing capabilities of the Cloud. Alternatively, the Cloud is provided as a service such that it is physically located at a location separate from the user, and the service provided is the storing and processing of data.

It will be understood that the embodiments described herein are not limited in their application to the details of the teachings and descriptions set forth, or as illustrated in the accompanying figures. Rather, it will be understood that an oral screening toothbrush, as taught and described according to multiple embodiments disclosed herein, is capable of other embodiments and of being practiced or carried out in various ways.

Also, it is to be understood that the phraseology and terminology used herein is for the purpose of description and should not be regarded as limiting. The use herein of "including," "comprising," "i.e.," "containing," or "having," and variations of those words is meant to encompass the items listed thereafter, and equivalents of those, as well as additional items.

Accordingly, the descriptions herein are not intended to be exhaustive, nor are they meant to limit the understanding of the embodiments to the precise forms disclosed. It will be understood by those having ordinary skill in the art that modifications and variations of these embodiments are reasonably possible in light of the above teachings and descriptions.

What is claimed is:

1. An oral screening toothbrush, comprising:
   a handle;
   a brush head having a plurality of bristles;
   a neck that is arranged to be distal to the handle and proximal to the brush head;
   a data processing unit that is configured to store and process data;
   a transceiver that is configured to transmit data;
   at least one light-emitting diode that is configured to emit light into the oral cavity; and
   at least one photo detector that is located on an external surface of the toothbrush and configured to receive the emitted light that is reflected from the surface of the oral cavity and transmit photographic data.

2. The oral screening toothbrush of claim 1, wherein the transceiver is further configured to receive data.

3. The oral screening toothbrush of claim 1, wherein at least one light-emitting diode is configured to emit blue light at a wavelength of 450-495 nanometers.

4. The oral screening toothbrush of claim 1, wherein the data processing unit is configured to control the intensity and activation of at least one light-emitting diode.

5. The oral screening toothbrush of claim 1, wherein multiple light-emitting diodes are configured in a cluster.

6. The oral screening toothbrush of claim 1, wherein the brush head comprises at least one light-emitting diode.

7. The oral screening toothbrush of claim 1, wherein the handle comprises at least one light-emitting diode.

8. The oral screening toothbrush of claim 1, wherein the neck comprises at least one light-emitting diode.

9. The oral screening toothbrush of claim 8, further comprising a waveguide that is configured to deliver light from at least one light-emitting diode to the exterior of the oral screening toothbrush.

10. The oral screening toothbrush of claim 1, wherein the photo detector is selected from the group consisting of an active pixel sensor, a charge-coupled device, a reverse-biased LED, a photoresistor, a photovoltaic cell, a phototransistor, and a quantum dot photo detector, or any combination thereof.

11. The oral screening toothbrush of claim 1, wherein the photo detector is an active pixel sensor comprising a complementary metal-oxide-semiconductor (CMOS) sensor.

12. The oral screening toothbrush of claim 1, wherein the photo detector is configured to couple to at least one optical fiber.

13. The oral screening toothbrush of claim 1, wherein the photo detector transmits photographic data to the data processing unit that is configured to process the photographic data for oral conditions.

14. The oral screening toothbrush of claim 13, wherein the oral condition is selected from the group consisting of oral cancer and dental caries, or any combination thereof.

15. An oral screening system, comprising:
    an oral screening toothbrush having a handle, a brush head with a plurality of bristles, a data processing unit that is configured to store and process data, a transceiver that is configured to transmit data, at least one light-emitting diode that is configured to emit light into the oral cavity, and at least one photo detector that is located on an external surface of the toothbrush and configured to receive the emitted light that is reflected from the surface of the oral cavity and transmit photographic data; and
    a cloud computing network having at least one data processing unit that is configured to store and process data and a transceiver that is configured to receive data,
    wherein the transceiver of the oral screening toothbrush is configured to transmit photographic data and the transceiver of the cloud computing network is configured to receive the photographic data.

16. An oral screening system, comprising:
    an oral screening toothbrush having a handle, a brush head with a plurality of bristles, a data processing unit that is configured to store and process data, a transceiver that is configured to transmit data, at least one light-emitting diode that is configured to emit light into the oral cavity, and at least one photo detector that is located on an external surface of the toothbrush and configured to receive the emitted light that is reflected from the surface of the oral cavity and transmit photographic data;
    a cloud computing network having at least one data processing unit that is configured to store and process data and a transceiver that is configured to receive and transmit data; and
    a data transfer medium having a transceiver that is configured to receive and transmit data, a data processing unit that is configured to store and process data, and a display medium that is configured to display data.

17. The oral screening system of claim 16, wherein the transceiver of the oral screening toothbrush is configured to transmit photographic data, the transceiver of the data transfer medium is configured to receive photographic data, and the data processing unit of the data transfer medium is configured to process the photographic data for oral conditions.

18. The oral screening system of claim 16, wherein the data transfer medium further comprises at least one photo detector that is configured to receive emitted light that is reflected from the surface of the oral cavity and transmit photographic data.

19. The oral screening system of claim 18, wherein the data processing unit of the data transfer medium is configured to process the photographic data for oral conditions.

* * * * *